United States Patent [19]

Weber et al.

[11] 4,013,713
[45] Mar. 22, 1977

[54] DIARYLVINYL-DIHYDROPHENANTHRENE COMPOUNDS

[75] Inventors: Kurt Weber; Christian Lüthi, both of Basel, Switzerland

[73] Assignee: Ciba-Geigy Corporation, Ardsley, N.Y.

[22] Filed: Sept. 15, 1975

[21] Appl. No.: 613,697

Related U.S. Application Data

[63] Continuation of Ser. No. 316,804, Dec. 20, 1972, abandoned.

[52] U.S. Cl. .................. 260/505 R; 260/465 R; 260/473 F; 260/515 R; 260/515 A; 260/607 A; 260/611 A; 260/669 R; 8/1 W
[51] Int. Cl.[2] ................................. C07C 143/24
[58] Field of Search ........................ 260/505 R

[56] References Cited
UNITED STATES PATENTS 3,177,208   4/1965   Stilz et al. .................. 260/240

Primary Examiner—James O. Thomas, Jr.
Assistant Examiner—A. Siegel
Attorney, Agent, or Firm—Karl F. Jorda; Edward McC. Roberts; Prabodh I. Almaula

[57] ABSTRACT

New diarylvinyl-dihydrophenanthrene compounds of the formula

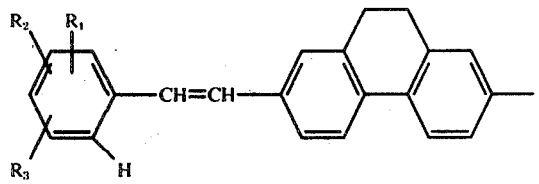

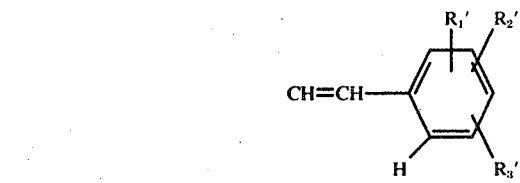

wherein $R_1$, $R_1'$, $R_2$, $R_2'$, $R_3$ and $R_3'$ are identical or different and represent hydrogen, alkyl with 1 to 12 carbon atoms, aralkyl with 1 to 4 carbon atoms in the alkyl part, alkoxy with 1 to 18 carbon atoms, phenylalkoxy with 1 to 4 carbon atoms in the alkoxy part, alkenyloxy with 3 to 4 carbon atoms, halogen, nitrile, a sulphonic acid group or its salts or functional derivatives, a carboxyalkoxy or carboxyl group or their salts or functional derivatives, or a sulphone group. These compounds are particularly useful as optical brighteners.

5 Claims, No Drawings

DIARYLVINYL-DIHYDROPHENANTHRENE COMPOUNDS

This is a continuation of application Ser. No. 316,804, filed on Dec. 20, 1972, now abandoned.

The present invention relates to new styryl derivatives of 9,10-dihydrophenanthrene, processes for their manufacture, and their use as optical brighteners for organic materials.

It has been found that a group of 2,7-diarylvinyl-9,10-dihydrophenanthrenes include valuble optical brighteners. The new compounds correspond to the general formula

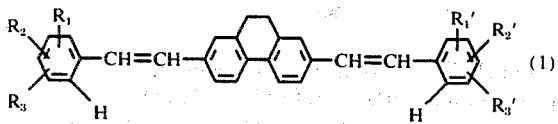

wherein $R_1$, $R_1'$, $R_2$, $R_2'$ and $R_3$ as well as $R_3'$ are identical or different and denote hydrogen, alkyl with 1 to 12 C atoms, aralkyl with 1-4 C atoms in the alkyl part, alkoxy with 1-18 C atoms, phenyl-(1-4C)-alkoxy, alkenyloxy with 3-4 C atoms, halogen, the sulpho group, including its salts and functional derivatives, the carboxyalkoxy or carboxyl group, including its salts and functional derivatives, nitrile or a sulphone group.

In the above context, the preferred halogen is chlorine. By sulpho groups and carboxyl groups there are to be understood both the free acids and their salts, with the water-soluble salts, such as alkali salts, ammonium salts and amine salts being of particular interest. In both cases, functional derivatives to be mentioned are above all the esters with 1-18 C atoms (alkyl esters, alkenyl esters, aralkyl esters (for example benzyl esters) and phenyl esters), as well as the amides, that is to say both the unsubstituted and the monosubstituted or disubstituted amides, such as, for example, the alkylamides, hydroxyalkylamides, cycloalkylamides, aralkylamides, phenylamides and morpholides, in each case normally with not more than 18 C atoms. Carboxyalkoxy radicals and their functional derivatives can have the carboxyl grouping modified analogously; the alkoxy bridge member can contain up to 5 C atoms. Possible sulphone groups are arylsulphones, for example phenylsulphonyl and preferably alkylsulphonyl with 1 to 18, especially 1 to 4, C atoms.

Compounds of preferred interest are characterised by the formulae listed below:

a. Compounds of the formula

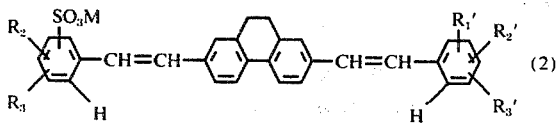

wherein $R_2$, $R_3$, $R_1'$, $R_2'$ and $R_3'$ are identical or different and denote hydrogen, alkyl with 1-12 C atoms, aralkyl with 1-4 C atoms in the alkyl part, alkoxy with 1-18 C atoms, phenyl-(1-4 C)-alkoxy, alkenyloxy with 3-4 C atoms, halogen, the sulpho group, including its salts and functional derivatives, the carboxyalkoxy or carboxyl group, including their salts and functional derivatives, nitrile or a sulphone group and wherein M represents a hydrogen ion or a salt-forming cation.

b. Compounds of the formula

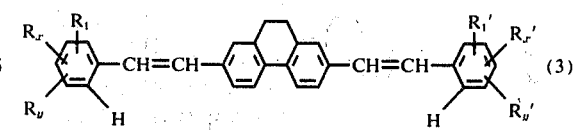

wherein $R_1$ and $R_1'$ are identical or different and denote hydrogen, alkyl with 1 to 12 carbon atoms, alkoxy with 1 to 18 carbon atoms, phenyl-(1-4 C)-alkoxy, alkenyloxyl with 1 to 4 carbon atoms, halogen, the sulpho group, including its salts and functional derivatives, the carboxyalkoxy or carboxyl group, including its salts and functional derivatives, nitrile or a sulphone group, $R_x$ and $R_x'$ are identical or different and denote hydrogen, chlorine, alkyl with 1 to 4 carbon atoms or the sulpho group, including its salts, and $R_y$ and $R_y'$ are identical or different and denote hydrogen, chlorine or methyl.

c. Compounds of the formula

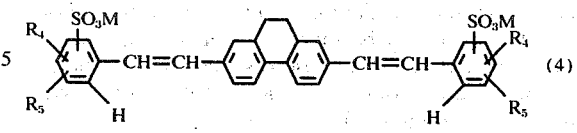

wherein $R_4$ denotes hydrogen, a $-SO_3M$ group, an alkyl group with 1-4 C atoms, an alkoxy group with 1-4 C atoms or chlorine, $R_5$ denotes hydrogen, an alkyl group with 1-4 C atoms, an alkoxy group with 1-4 C atoms or chlorine and M represents a hydrogen ion or a salt-forming cation.

d. Compounds of the formula

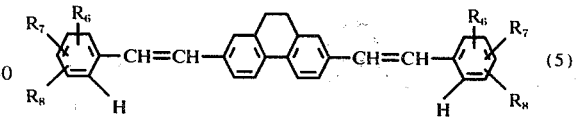

wherein $R_6$ denotes hydrogen, an alkyl group with 1-4 C atoms, chlorine, alkoxy with 1-4 C atoms, a carboxyl-alk($C_1$ to $C_3$)-oxy or carboxyl group, including their alkali metal, alkali earth metal and amine salts, esters and amides with up to 12 C atoms, a sulphonic acid ester or amide group with 1-12 C atoms, a sulphone group, nitrile, an alkenyloxy group with 3-4 C atoms or a benzyloxy group, $R_7$ represents hydrogen, alkoxy with 1-4 C atoms, alkyl with 1-4 C atoms or chlorine and $R_8$ represents hydrogen, alkyl with 1-4 C atoms or chlorine.

e. Compounds of the formula

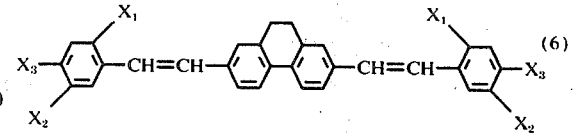

wherein $X_1$ denotes hydrogen, chlorine or $-SO_3M_1$, $X_2$ differs from $X_1$ and denotes hydrogen, chlorine or $-SO_3M_1$, $X_3$ denotes hydrogen or chlorine and $M_1$ represents a hydrogen ion or an alkai metal, alkaline earth metal or ammonium cation.

f. Compounds of the formula

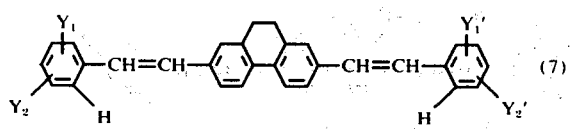

wherein $Y_1$ and $Y_1'$ are identical or different and denote hydrogen, the sulpho group or its Na or K salt, chlorine, carbomethoxy, nitrile or methyl and $Y_2$ and $Y_2'$ are identical or different and denote hydrogen, chlorine or methyl.

g. Compounds of the formula

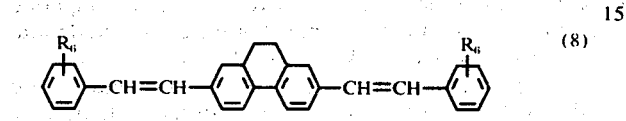

wherein $R_6$ has the meaning indicated under the formula (5).

The compounds of the formula (1) and of the subordinate formulae can be manufactured analogously to methods which are in themselves known. In general, the procedure followed is to react about 1 mol equivalent of a compound of the formula

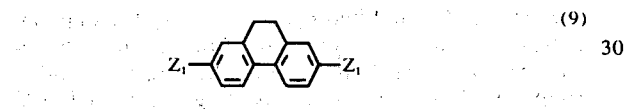

with about 1 mol equivalent of a compound of the formula

and about 1 mol equivalent of a compound of the formula

with one of the symbols $Z_1$ and $Z_2$ denoting an O=CH— group and the other denoting one of the groupings of the formulae

-continued
and $$-CH=\overset{R}{\underset{R}{\overset{|}{P}}}-R \qquad (15)$$

wherein R represents an alkyl radical which is optionally substituted further, preferably an alkyl radical with up to 6 carbon atoms, an aryl radical, preferably a phenyl radical, a cycloalkyl radical, preferably a cyclohexyl radical, or an aralkyl radical, preferably a benzyl radical.

In an entirely analogous manner a. compounds of the formula (2) are obtained by reaction of about 1 mol equivalent of a compound of the formula

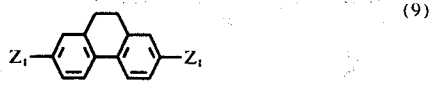

with about 1 mol equivalent of a compound of the formula (16)

and about 1 mol equivalent of a compound of the formula (11)

b. a compound of the formula (3) is obtained by reaction of about 1 mol equivalent of a compound of the formula (9)

with about 1 mol equivalent of a compound of the formula

and about 1 mol equivalent of a compound of the formula

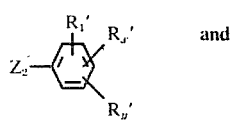 and (18)

c. compounds of the formula (4) are obtained by reaction of about 1 mol equivalent of a compound of the formula

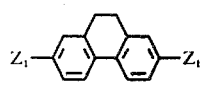 (9)

with about 2 mol equivalents of a compound of the formula

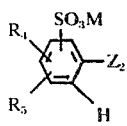 (19)

with the symbols $Z_1$ and $Z_2$ having the abovementioned meaning.

Thus, for example, dialdehydes of the formula

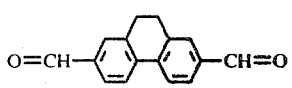 (20)

can be reacted with monofunctional compounds of the formula

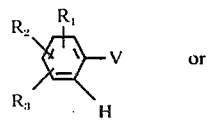 (21)

or

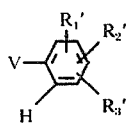 (22)

or monoaldehydes of the formula

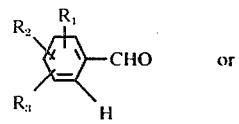 (23)

or

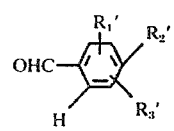 (24)

can be reacted with bifunctional compounds of the formula

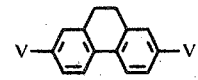 (25)

wherein the R-symbols have the indicated meaning and V denotes one of the phosphorus-containing substituents of the formulae (12) to (15).

The phosphorus compounds of the formula (21), (22) and (25) which are here required as starting substances are obtained in a manner which is in itself known by reacting halogenomethyl compounds, preferably chloromethyl or bromomethyl compounds, of the formula

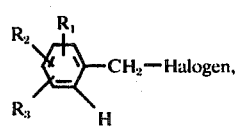 (26)

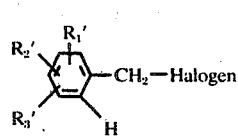 (27)

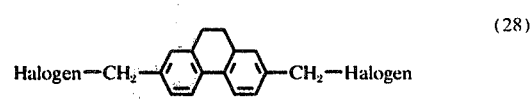 (28)

with phosphorus compounds of the formulae

 (29)

 (30)

 or (31)

 (32)

In these formulae, R has the indicated meaning, and radicals R bonded to oxygen are preferably lower alkyl groups whilst radicals R directly bonded to phssphorus are preferably aryl radicals, such as benzene radicals.

To manufacture compounds according to the formula (1) it is in particular possible to use those of the abovementioned process variants according to which about 1 mol equivalent of a compound of the formula

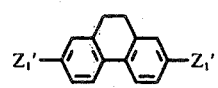 (33)

is reacted with about one mol equivalent each of a compound of the formula

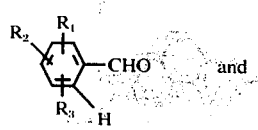 (34)

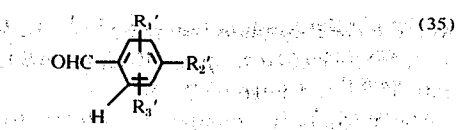 (35)

with $R_1$, $R_2$, $R_3$, $R_1'$, $R_2'$ and $R_3'$ having the abovementioned meaning and $Z_1$ denoting a grouping of the formulae

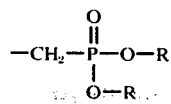 (12)

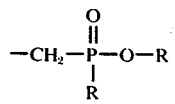 (13)

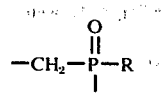 (14)

and

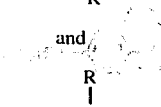 (15)

wherein R represents an optionally substituted alkyl, cycloalkyl, aryl or aralkyl radical.

A variant of particular practical importance consists of using, as the dihydrophenanthrene components according to the formula (9), those which correspond to the formula

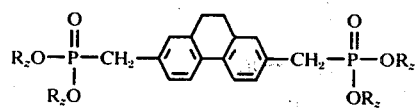 (36)

wherein $R_z$ denotes an alkyl group with 1 to 6 atoms.

The manufacturing process is advantageously carried out in inert solvents. As examples thereof there may be mentioned hydrocarbons such as toluene and xylene or alcohols such as methanol, ethanol, isopropanol, butanol, glycols, glycol-ethers such as 2-methoxyethanol, hexanols, cyclohexanol and cyclooctanol, and also ethers such as diisopropyl ether, tetrahydrofurane and dioxane, as well as dimethylsulphoxide, formamide and N-methylpyrrolidone. Polar organic solvents such as dimethylformamide and dimethylsulphoxide are particularly suitable. Some of the reactions can also be carried out in aqueous solution.

The temperature at which the reaction is carried out can vary within wide limits. It is determined ($\alpha$) by the stability of the solvent used towards the reactants, especially towards the strongly basic alkali metal compounds, ($\beta$) by the reactivity of the condensation partners and ($\gamma$) by the activity of the combination of solvent-base as the condensation agent.

Accordingly, in practice temperatures between about 10° and 100° C are in general used, especially if dimethylformamide or dimethylsulphoxide are used as solvents. The preferred temperature range is about 20° to 60° C. However, under certain circumstances higher temperatures can also be used if this is desired for reasons of saving time or a less active but cheaper condensation agent is to be employed. Fundamentally, reaction temperatures in the range of 10° to 180° C are thus also possible.

As strongly basic alkali metal compounds, the hydroxides, amides and alcoholates (preferably those of primary alcohols containing 1 to 4 carbon atoms) of the alkali metals are above all used, and for economic reasons those of lithium, sodium and potassium are of predominant interest. However, in principle, and in special cases, it is also possible successfully to use alkali metal sulphides and alkali metal carbonates, aryl-alkali metal compounds such as, for example, phenyl-lithium, or strongly basic amines (including ammonium bases, for examples trialkylammonium hydroxides).

The new compounds defined above show a more or less pronounced fluorescence in the dissolved or finely divided state. They can be used for the optical brightening of the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, cross-linking, grafting or degradation products, polymer blends, or products obtained by modification of reactive groups, and the like, for example polymers based on $\alpha$, $\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), and polymers based on vinyl and vinylidene compounds (such as, for example, vinyl alcohol), b. Polymerisation products such as are, for example, obtainable by ring opening, for example polyamides of the polycaprolactam type, and also polymers which are obtainable both via polyaddition and via polycondensation, such as polyethers or polyacetals, c. Polycondensation products or precondensates based on bifunctional of polyfunctional compounds possessing condensable groups, their homocondensation and co-condensation products, and after-treatment products, such as, for example, polyamides (for example hexamethylenediamine adipate), maleate resins, melamine resins, their precondensates and analogues, polycarbonates and silicones, d. Polyaddition products such as polyurethanes (cross-linked and non-crosslinked) and epoxide resins.

II. Semi-synthetic organic materials such as, for example, cellulose esters of varying degrees of esterification (acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, that is to say, for example, predominantly three-dimensional bodies such as sheets, profiles, injection mouldings, various machined articles, chips, granules or foams, and also as predominantly two-dimensional bodies such as film, foils, lacquers, coverings, impregnations and coatings, or as predominantly one-dimensional bodies such as filaments, fibers, blocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibers, flocks, hanks, textile filaments, yarns, threads, fiber fleeces, felts, waddings, flock structures or woven textile fabrics or textile laminates, knitted facrics as well as of papers, cardboards or paper compositions and the like.

The compounds to be used according to the invention are of importance, inter alia, for the treatment of organic textile materials, especially woven textile fabrics. Where fibers, which can be in the form of staple fibers or endless filaments or in the form of hanks, woven fabrics, knitted fabrics, fleeces, flock substrates or laminates, are to be optically brightened according to the invention, this is advantageously effected in an aqueous medium, wherein the compounds in question are present in a finely divided form (suspensions, or possibly solutions. If desired, dispersing agents, stabilisers, wetting agents and further auxiliaries can be added during the treatment. Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing processes in dyeing machines).

The new optical brighteners according to the present invention can further be added to, or incorporated into, the materials before or during their shaping. Thus they can for example be added to the compression moulding composition or injection moulding composition during the manufacture of films, sheets or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (for example white pigments), or as an additive to dye baths, printing pastes, discharge pastes or reserve pastes, or for the after-treatment of dyeings, prints or discharge prints, b. Mixed with so-called "carriers", wetting agents, plasticisers, swelling agents, anti-oxidants, light protection agents, heat stabilisers and chemical bleaching agents (bleaching bath additives), c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes or antistatic finishes, or antimicrobial finishes, d. Incorporation of the optical brighteners into polymeric carriers (polymerisation, polycondensationl or polyaddition products), in a dissolved or dispersed form, for use, for example, in coating agents, impregnating agents or binders (solutions, dispersions and emulsions) for textiles, fleeces, paper and leather, e. As additives to so-called "master batches", f. As additives to the most diverse industrial products in order to render these more marketable (for example improving the appearance of soaps, detergents, pigments and the like), g. In combination with other optically brightening substances, h. In spinning bath preparations, that is to say as additives to spinning baths such as are used for improving the slip for the further processing of synthetic fibers, or from a special bath before the esterification of the fibre, i. As scintillators for various purposes of a photographic nature, such as, for example, for electrophotographic reproduction or supersensitisation.

If the brightening process is combined with textile treatment methods of finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, with the brighteners according to the invention is to impregnate these fibres with the aqueous dispersions or solutions of the brighteners at temperatures below 75° C, for example at room temperature, and to subject them to a dry heat treatment at temperatures above 100° C., it being generally advisable additionally to dry the fibre material beforehand at a moderately elevated temperature, for example at not less than 60° C and up to about 130° C. The heat treatment in then dry state is then advantageously carried out at temperatures between 120° and 200° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within the wide limits. A distinct and durable effect is already achievable with very small amounts, in certain cases, for example, amounts of 0.0001 per cent by weight. However, amounts of up to 1% can also be employed. For most practical purposes, amounts between 0.005 and 0.5 per cent by weight are of preferred interest.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to the domestic or industrial washing agents in any stage of the manufacturing process of the washing agents, for example to the so-called "slurry" before spray-drying the washing powder, or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, syndet, (soluble salts of sulphonates of higher fatty alcohols), arylsulphonic acids with higher and/or multiple alkyl substituents, sulphocarboxylic acid esters of medium to higher alcohols, fatty acid acylaminoalkyl-or acylaminoaryl-glycerinesulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminotetraacetic acid, and foam stabilisers such as alkanolamides of higher fatty acids. The washing agents can further contain for example: antistatic agents, skin protection agents which restore fat, such as lanolin, enzymes, anti-microbial agents, perfumes and dyestuffs.

The new optical brighteners have the particular advantage that they are also active in the presence of active chlorine donors such as, for example, hypochlorite, and can be used without significant loss of the effects in wash liquors containing non-ionic washing agents, for example alkylphenol polyglycol ethers.

The compounds according to the invention are added in amounts of 0.01–1%, relative to the weight of the liquid or pulverulent finished washing agent. Washing liquors which contain the indicated amounts of the optical brighteners claimed impart a brilliant appearance in daylight when used to wash textiles of cellulose fibres, polyamide fibres, cellulose fibres with a high quality finish and the like.

The washing treatment is carried out as follows, for example:

The textiles indicated are treated for 1.30 minutes at 20° to 100° C in a wash liquor which contains 1 to 10 g./l of a built-up composite washing agent and 0.05 to 1%, relative to the weight of the washing agent, of the claimed brightening agents. The liquor ratio can be 1:3 to 1:50. After washing, the textiles are rinsed and dried in the usual manner. The wash liquor can contain 0.2 g/l of active chlorine (for example as hypochlorite) or 0.1 to 2 g/l of sodium perborate as a bleaching additive.

In the examples parts, unless otherwise stated, are always parts by weight, and percentages always percentages by weight. Unless othewise noted, melting points and boiling points are uncorrected.

Within the framework of the present invention it is also possible without difficulty — depending on the special applicational requirements — to employ the new asymmetrical compounds which have been described mixed with the corresponding compounds of symmetrical structure, obtainable from the competing reaction of the manufacturing process, for the purpose of optical brightening. This means that in the practice of applying the compounds it is also possible — depending on the end use — to dispense with separating the competing reaction products. If appropriate, a symmetrical water-insoluble compound can be separated off, whilst a mixture of the water-soluble compounds is employed for the purpose of optical brightening.

If desired, the reaction can be conducted in such a way, in order to reduce the proportion of a symmetrical water-insoluble compound in the reaction mixture, that per mol equivalent of the bifunctional reaction component employed a total of about two mol equivalents of monofunctional reaction components are employed; at the same time, the ratio of component containing sulphone groups to component free of sulphone can lie approximately in the molar ratio of between 1 : 1 and 10 : 1.

EXAMPLE 1

7.2 g of 2,7-bis-(diethoxyphosphonomethyl)-9,10-dihydro-phenanthrene of the formula

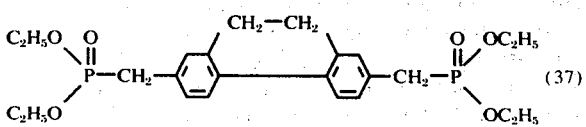

(37)

and 3.3 g of benzaldehyde (content: 96%) are dissolved in 150 ml of anhydrous dimethylformamide at 40° C whilst stirring and displacing the air by nitrogen. 2.2 g of sodium methylate (content: 98.4%) are introduced over the course of about 5 minutes at 40°–45° C. The mixture is stirred for a further 3 hours at 40°–45° C, cooled to room temperature, diluted with 150 ml of desalinated water and neutralised with a little formic acid and the product which has crystallised out is filtered off, washed with methanol until the filtrate issues colourless and clear and dried in vacuo at 80°–85° C. About 2.6 g of the compound of the formula

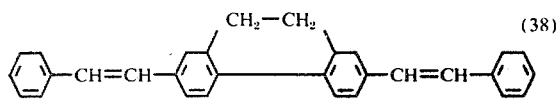 (38)

are obtained; melting point 248°–252° C. Recrystallisation from 65 ml of dioxane, with addition of active charcoal, yields 1.6 g of the compound (38) as a pale yellow crystal powder of melting point 262°–263° C.

To manufacture the compound (38) it is equally possible to employ, instead of the 2,7-bis-(diethoxyphosphonomethyl)-9,10-dihydro-phenanthrene of the formula (37) which has been used, the equivalent amount of the 2,7-bis-(dimethoxyphosphonomethyl)-9,10-dihydrophenanthrene of the formula

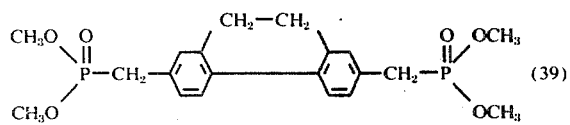 (39)

Equally, dimethylsulphoxide can be used as the solvent instead of dimethylformamide. Finally, potassium hydroxide powder or sodium hydroxide powder can be used as alkaline condensation agents instead of sodium methylate. The compound of the formula (38) can be obtained in a similar manner to that described, by reacting the dialdehyde of the formula

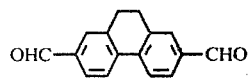 (40)

with 2 mol equivalents of the phosphonate of the formula

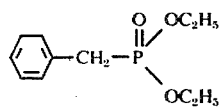 (41)

The dialdehyde of the formula (40) can be obtained as follows: 7 g of sodium metal are dissolved in 350 ml of absolute ethanol whilst stirring. 32.1 g of 2-nitropropane are then added dropwise and thereafter 38.8 g of 2,7-bis-chloromethyl-9,10-dihydrophenanthrene are introduced. The reaction mixture is then heated to the boil and boiled under reflux for 4 hours. After cooling to 20° C, the product which has crystallised out is filtered off and first washed with ethanol, then with water and again with alcohol. After drying in vacuo at 60°–65° C, 23.0 g of the dialdehyde of the formula (40), of melting point 160°–163° C, are obtained. After recrystallisation from 150 ml of dioxane with addition of active charcoal, 13.6 g of the dialdehyde of the formula (40) are obtained as a crystal powder of melting point 162°–163° C.

The phosphonate of the formula (41) can be obtained by reaction of benzyl chloride with an excess of triethylphosphite at 140°–145° C.

2,7-Bis-(diethoxyphosphonomethyl)-9,10-dihydrophenanthrene of the formula (37) can be obtained as follows: 60 g of 2,7-bis-chloromethyl-9,10-dihydrophenanthrene are introduced in portions over the course of 20 minutes into 200 ml of triethylphosphite at 120°–125° C whilst stirring. After the introduction, the mixture is heated to 140° C and stirred for 2 hours at 140°–145° C, in the course of which ethyl chloride distils off. The excess triethylphosphite is distilled off under normal pressure. About 95 g of the compound of the formula (37) are obtained as a viscous liquid which solidifies to crystals after about one week. If instead of triethylphosphite trimethylphosphite is used and the reaction is carried out at approx. 115° C, 2,7-bis-(dimethoxyphosphonomethyl)-9,10-dihydrophenanthrene of the formula (39) is obtained.

EXAMPLE 2

7.2 g of 2,7-bis-(diethoxyphosphonomethyl)-9,10-dihydrophenanthrene and 4.4. g of o-chlorobenzaldehyde (content: 96.6%) are reacted according to Example 1. 3.6 g of the compound of the formula

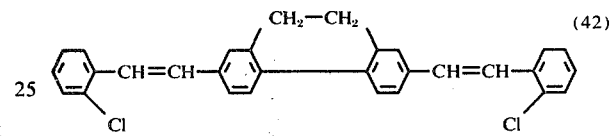 (42)

are obtained; melting point: 147°–152° C. After recrystallisation from 50 ml of dioxane, using active charcoal, 1.2 g of the compound (42) are obtained as a pale yellow crystal powder of melting point 179°– 180° C.

If instead of 4.4 g of o-chlorobenzaldehyde 5.2 g of m-carbomethoxybenzaldehyde are employed and instead of the dimethylformamide dimethylsulphoxide is employed, and in other respects the procedure described in Example 1 is followed, 1.6 g of the compound of the formula

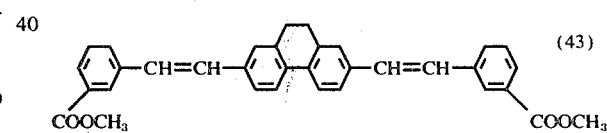 (43)

of melting point 175°– 177° C are obtained after recrystallisation from ethyl acetate.

EXAMPLE 3

9.6 g of 2,7-bis-(diethoxyphosphonomethyl)-9,10-dihydrophenanthrene and 15.0 g of the sodium salt of benzaldehyde-3-sulphonic acid (content: 61.3%) are reacted with 2.9 g of sodium methylate (content: 98.4%) in accordance with Example 1. After a reaction time of two hours, the reaction mixture is neutralised with formic acid and then evaporated to dryness. The residue is dissolved in 200 ml of boiling desalinated water, the solution is treated with about 1 g of active charcoal and filtered hot, 300 ml of ethanol are added to the hot clear filtrate, the mixture is cooled to about 5° C and the product which has crystallised out is filtered off. The product is dissolved in 100 ml of dimethylformamide, the solution is clarified by filtration and evaporated to dryness, the residue is dissolved in 50 ml of desalinated water, the solution is clarified by filtration and evaporated to dryness, and the residue is dried in vacuo at 100° –110° C.

2.5 g of the compound of the formula

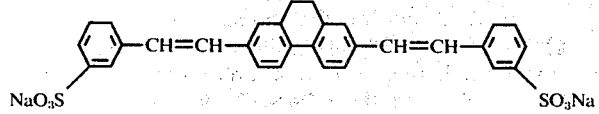

(44)

are thus obtained as a pale yellow powder. On dissolving the compound of the formula (44) in desalinated water and treating the solution with a strongly acid ion exchanger, the compound of the formula (44) is obtained as the free sulphonic acid. From this the potassium, lithium, ammonium, pyridinum, methylammonium, and dimethylammonium salts and the like, for example, are obtained by neutralisation with the appropriate bases. On adding, for example, barium chloride or calcium chloride to the solution of the sodium salt in water, the sparingly soluble barium or calcium salts of the compound of the formula (44) are obtained.

EXAMPLE 4

9.6 g of 2,7-bis-(diethoxyphosphonomethyl)-9,10-dihydrophenanthrene and 12.0 g of the sodium salt of 4-chlorobenzaldehyde-3-sulphonic acid (content 89.1%) are reacted analogously to Example 3. After a reaction time of 3 hours the reaction mixture is diluted with 600 ml of desalinated water, neutralised with a little formic acid, heated to the boil, treated with about 2 g of active charcoal and clarified by filtration, and 30 g of sodium chloride are added to the clear filtrate. The mixture is then allowed to cool to room temperature and the product which has crystallised out is filtered off and recrystallised from a mixture of 200 ml of desalinated water and 200 ml of ethanol. After drying in vacuo at 100° –110° C, 2.4 g of the compound of the formula

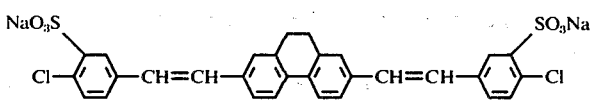

are obtained as a pale yellow crystal powder. The sodium salt of 4-chlorobenzaldehyde-3-sulphonic acid which was employed can be obtained by sulphonation of 4-chlorobenzaldehyde with oleum of 66% SO₃ content at 60°– 65° C.

EXAMPLE 5

9.6 g of 2,7-bis-(diethoxyphosphonomethyl)-9,10-dihydrophenanthrene and 12.3 g of the sodium salt of 2-chlorobenzaldehyde-5-sulphonic acid (content: 86.8%) are reacted analogously to Example 4. At the end of the reaction time the reaction mixture is filtered, the residue (inorganic salts) is washed with dimethylformamide and the filtrate together with the dimethylformamide used for washing is evaporated to dryness. The product is dissolved in 300 ml of boiling desalinated water, the solution is treated with about 2 g of active charcoal and clarified by filtration and 7.5 g of sodium chloride are added to the clear filtrate. It is then allowed to cool to room temperature and the product which has crystallised out is filtered off and recrystallised from a mixture of 700 ml of ethanol and 50 ml of desalinated water. After drying in vacuo at 100° –110° C, 0.7 g of the compound of the formula

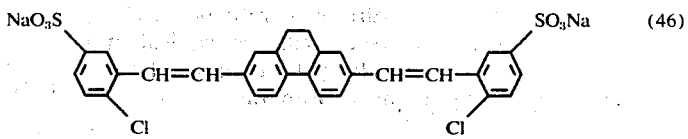

(46)

are thus obtained as a yellow crystal powder.

EXAMPLE 6

12.7 g of 2-cyano-benzylphosphonic acid diethyl ester and 5.9 g of 9,10-dihydrophenanthrene-2,7-dialdehyde are dissolved in 100 ml of anhydrous dimethylformamide at 55° whilst stirring and displacing the air by nitrogen. After cooling to 40° C, 3.8 g of sodium methylate (content: 99.2%) are introduced over the course of about 3 minutes. The temperature is kept below 45°, C by cooling with icewater. The reaction mixture is stirred for a further 3 hours at 40° –45° C and then cooled to 2° C, and the product which has crystallised out is filtered off and first washed with 40 ml of dimethylformamide, then with 100 ml of methanol and finally with 100 ml of water. After drying in vacuo at 90° –100° C, 7.3 g of the compound of the formula

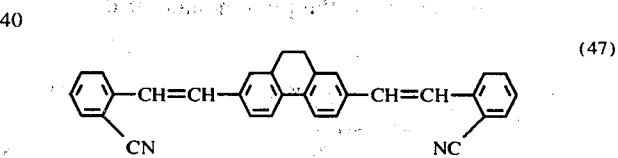

(47)

(45)

are obtained as a yellow crystal powder of melting point: 241°–243° C. On recrystallisation from 1,000 ml of tetrachloroethylene, with the aid of fuller's earth, 5.7 g of the compound of the formula (47), of melting point 243°–244°, are obtained.

In a similar manner to that described in the preceding examples, the compounds of the formula

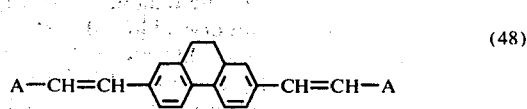

(48)

listed in Table I below are obtained on using the appropriate aldehydes and phosphonomethyl derivatives.

Compounds of this formula (48) which contain functionally modified carboxylic acid groups or sulphonic acid groups are appropriately obtained by subsequent reaction of the free acids or their salts in accordance with known methods, for example by suspending them in a solvent such as chlorobenzene and first converting them with thionyl chloride, in the presence of catalytic amounts of pyridine or dimethylformamide, into the corresponding acid chlorides which are then subsequently converted into the desired esters or amides by means of alcohols, phenols or amines (primary or secondary).

Table I

| No. | A |
|---|---|
| 49 | —C₆H₄—SO₃Na (2-) |
| 50 | —C₆H₄—Cl (3-) |
| 51 | —C₆H₄—Cl (4-) |
| 52 | —C₆H₄—CH₃ (3-) |
| 53 | —C₆H₄—CN (3-) |
| 54 | —C₆H₄—OCH₃ (3-) |
| 55 | —C₆H₃(CH₃)(SO₃Na) |
| 56 | —C₆H₃(OCH₃)(SO₃K) |
| 57 | —C₆H₄—C(CH₃)₃ (4-) |
| 58 | —C₆H₄—OCH₂CH₂CH₂CH₃ (3-) |
| 59 | —C₆H₄—OCH₂COONa (3-) |
| 60 | —C₆H₄—OCH₂CH₂CH₂COOH (3-) |

Table I-continued

| No. | A |
|---|---|
| 61 | —C₆H₄—OCH₂CH₂CH₂COOC₈H₁₇(n) (3-) |
| 62 | —C₆H₄—OCH₂CONHC₄H₉(n) (3-) |
| 63 | —C₆H₄—COONa (2-) |
| 64 | —C₆H₄—CON(CH₂CH₂CH₃)₂ (2-) |
| 65 | —C₆H₄—COOCH₂CH(C₂H₅)(C₄H₉) (2-) |
| 66 | —C₆H₄—SO₂O—C₆H₅ (3-) |
| 67 | —C₆H₄—SO₂NH₂ (3-) |
| 68 | —C₆H₄—SO₂NHCH₂CH₂OH (3-) |
| 69 | —C₆H₄—SO₂N(CH₂CH₂OH)₂ (3-) |
| 70 | —C₆H₄—SO₂CH₃ (4-) |
| 71 | —C₆H₄—OCH₂—CH=CH₂ (3-) |
| 72 | —C₆H₄—OCH₂—C₆H₅ (3-) |
| 73 | —C₆H₃Cl₂ (2,4-) |
| 74 | —C₆H₃Cl₂ (3,4-) |

Table I-continued

| No. | A |
|---|---|
| 75 | 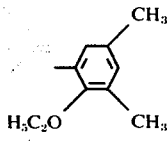 |
| 76 | 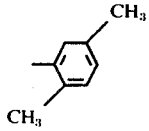 |
| 77 | 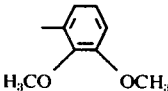 |
| 78 | 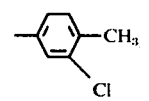 |
| 79 | 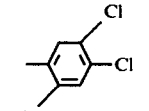 |
| 80 | 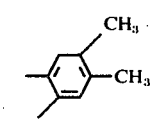 |
| 81 | 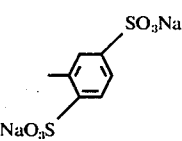 |

EXAMPLE 7

24.0 g of 2,7-bis-(diethoxyphosphonomethyl)-9,10-dihydrophenanthrene, 17.0 g of the sodium salt of benzaldehyde-3-sulphonic acid (content: 61.3%) and 7.3 g of o-chlorobenzaldehyde (content: 96.6%) are reacted with 7.1 g of sodium methylate in accordance with Example 1. After a reaction time of three hours, the reaction mixture is neutralised with a little formic acid and evaporated to dryness. A mixture of the compounds of the formula

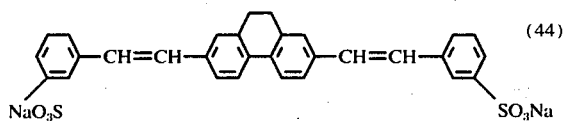

(44)

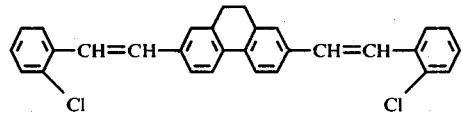

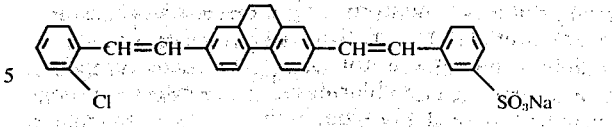

is thus obtained. This mixture can frequently be used, without further separation, for the brightening of organic materials. A separation of the mixture is carried out on the basis of the differing solubilites of the individual components.

EXAMPLE 8

9.6 g of 2,7-bis-(diethoxyphosphonomethyl)-9,10-dihydrophenanthrene, 4.3 g of benzaldehyde-2-sulphonic acid (as the sodium salt, 97.6% content) and 2.6 g of m-cyanobenzaldehyde are reacted in 20 ml of anhydrous dimethylformamide, together with 30 g of sodium methylate, in accordance with the instructions in Example 1. In order to workup and separate the mixture, 75 ml of water are added at the end of the reaction and the excess alkali is neutralised with a few drops of acetic acid. The material which has precipitated is filtered off and rinsed with 25 ml of water. The filtrate contains the compound of the formula

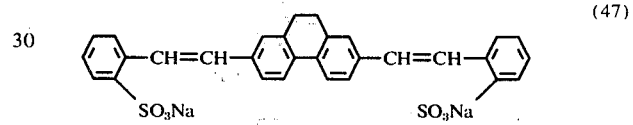

(47)

which can be isolated by salting-out with sodium chloride.

The filter residue is dried, powdered and extracted three times with 500 ml of hot toluene at a time. The combined extracts are treated with 0.5 g of fuller's earth, concentrated to 150 ml and treated with n-hexane at the boil until cloudy. After cooling in ice, the precipitate is filtered off and dissolved, whilst still moist, in 50 ml of dimethylformamide, apart from a slight cloudiness, and the solution is clarified by filtration and then cooled. It is diluted with 50 ml of ethanol and cooled in ice, the product is filtered off and after drying 0.9 g of the compound of the formula

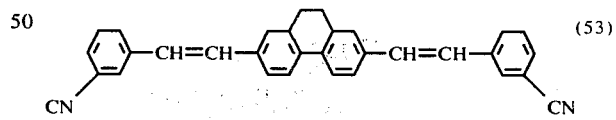

(53)

is obtained; melting point: 253° –255° C.

The residue from the toluene extraction mainly contains the asymmetrical compound of the formula

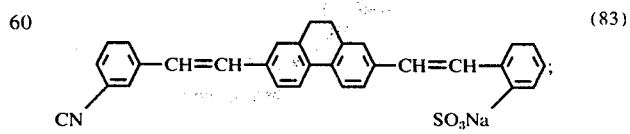

(83)

this is purified by dissolving in 500 ml of hot water, except for a slight cloudiness; the solution is clarified by filtration and concentrated to 250 ml. After cooling in ice, the product is filtered off and dried. 3.35 g of the above compound, which decomposes above 270° C, are thus obtained.

Analogously to Examples 7 and 8, the use of the appropriate aldehydes results in the formation of the asymmetrical compounds listed in Table II below (together with the corresponding symmetrical derivatives), of the formula

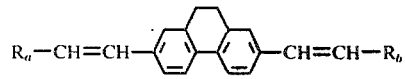 (84)

R$_a$—CH=CH—[stilbene]—CH=CH—R$_b$

Table II

| No. | R$_a$ | R$_b$ |
|---|---|---|
| 85 | phenyl-SO$_3$Na (meta) | phenyl |
| 86 | phenyl-SO$_3$K (meta) | phenyl |
| 87 | phenyl-SO$_3$Na (meta) | phenyl-Cl (para) |
| 88 | phenyl-SO$_3$Na (meta) | phenyl-C(CH$_3$)$_3$ (para) |
| 89 | phenyl-SO$_3$Na (meta) | phenyl-OCH$_2$CH$_2$CH$_2$CH$_3$ (para) |
| 90 | phenyl-SO$_3$Na (meta) | phenyl-SO$_3$Na (ortho) |
| 91 | phenyl-COOC$_2$H$_5$ (meta) | phenyl-SO$_3$K (ortho) |
| 92 | Cl, SO$_3$Na — phenyl | phenyl |
| 93 | NaO$_3$S, Cl — phenyl | phenyl |
| 94 | NaO$_3$S, SO$_3$Na — phenyl | phenyl-Cl |
| 95 | phenyl-SO$_3$Na (ortho) | phenyl-Cl |
| 96 | NaO$_3$S, SO$_3$Na — phenyl | phenyl-OCH$_3$ |

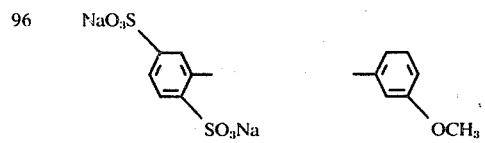

EXAMPLE 9

Bleached cotton fabric is washed for 15 minutes, using a liquor ratio of 1:20, in a liquor at 60° C which has the following composition per liter:
 0.004 g of one of the brighteners of the formula (44), (45), (46), (49) or (55)
 0.25 g of active chlorine (bleach solution)
 4 g of a washing powder of the following composition:
  15.00% of dodecylbenzenesulphonate
  10.00% of sodium lauryl sulphonate
  40.00% of sodium tripolyphosphate
  25.75% of anhydrous sodium sulphate
  7.00% of sodium metasilicate
  2.00% of carboxymethylcellulose and
  0.25% of ethylenediamine tetraacetic acid.

Here, the cotton fabric is only introduced into the path 15 minutes after the wash bath, at 60° C, has been prepared. After rinsing and drying, the fabric shows a good brightening effect of good fastness to acid, light and chlorine.

A good brightening effect is also achieved if the washing process is carried out in the same manner for 15 minutes at 30° C.

It is also possible directly to incorporate the brighteners of the formulae (44), (45), (46), (49) or (55) into the washing powder of the abovementioned composition.

EXAMPLE 10

A polyamide fibre fabric (Perlon-Helanca) is washed, using a liquor ratio of 1:20, for 15 minutes in a liquor at 55° C which contains the following additives per liter:
 0.004 g of one of the brighteners of the formulae (44), (45), (46), (49), (55), (83), (85), (92) or (95)
 0.25 g of active chlorine (bleach solution)
 4 g of a washing powder of the following composition:
  15.00% of dodecylbenzenesulphonate
  10.00% of sodium lauryl sulphonate
  40.00% of sodium tripolyphosphate
  25.75% of anhydrous sodium sulphate
  7.00% of sodium metasilicate
  2.00% of carboxymethylcellulose and
  0.25% of ethylenediamine tetraacetic acid.

The polyamide fibre fabric is only introduced into the wash bath at 55° C 15 minutes after the latter has been prepared. After rinsing and drying, the fabric shows a good brightening effect of good fastness to light.

A good brightening effect is als obtained if the wasing process is carried out in the same manner but at 25° C.

The washing powder of the abovementioned composition can contain the brighteners of the formulae (44), (45), (46), (49) (55), (83), (85), (92) or (95) directly incorporated into it.

EXAMPLE 11

A polyamide fibre fabric (Perlon) is introduced, using a liquor ratio of 1:40 into a bath at 60° C which contains (relative to the weight of the fabric) 0.1% of one of the brighteners of the formulae (44) to (46), (49), (55), (81), (83), (85), (92) or (95) and, per liter, 1 g of 80% strength acetic acid and 0.25 g of an addition product of 30 to 35 mols of ethylene oxide to one mol of technical stearyl alcohol. The bath is warmed to the boil over the course of 30 minutes and kept at the boil for 30 minutes. After rinsing and drying, a good brightening effect is obtained.

If instead of the fabric of polyamide-6 a fabric of polyamide-66 (nylon) is used, similar brightening effects are obtained.

Finally, it is also possible to work under high temperature conditions, for example, for 30 minutes at 130° C. For this type of use, it is advisable to add 3 g/l of hydrosulphite to the liquor.

EXAMPLE 12

A cotton article provided with a non-iron finish by means of an aminoplast resin is washed, using a liquor ratio of 1:20, for 15 minutes in a liquor at 60° C which contains the following additives per liter: 0.004 to 0.016 g of one of the brighteners of the formulae (44), (83), (85), (92) or (95)
  g of a washing powder of the following composition:
  15.00% of dodecylbenzenesulphonate
  10.00% of sodium lauryl sulphonate
  40.00% of sodium tripolyphosphate
  25.75% of anhydrous sodium sulphate
  7.00% of sodium metasilicate
  2.00% of carboxymethylcellulose and
  0.255 of ethylenediamine tetraacetic acid.
After rinsing and drying, the fabric shows a higher degree of whiteness in daylight than does the untreated material.

EXAMPLE 13

Bleached cotton fabric is washed for 15 minutes at 60° to 95° C, using a liquor ratio of 1:20. The washing material contains the following additives per liter:
  0.004 g of the brightener of the formula (44), (45) or (46) 4 g of a washing powder of the following composition:
  40.0% of soap flakes
  15.0% of sodium tripolyphosphate
  8.0% of sodium perborate
  1.0% of magnesium silicate
  11.0% of sodium metasilicate (9 $H_2O$)
  24.6% of calcined sodium carbonate
  0.4% of ethylenediaminetetraacetic acid
After rinsing and drying, the cotton fabric shows a strong brightening effect.

EXAMPLE 14

A bleached cotton fabric is introduced, using a liquor ratio of 1:25, into a bath at 20° C which contains (relative to the weight of the fabric) 0.1% of the brightener of the formula (44) or (49). The bath is warmed to 50° C over the course of 15 minutes and 5 g of crystalline sodium sulphate are then added per liter of liquor. After a further 15 minutes, the fabric is briefly rinsed and subsequently dried. The cotton treated in this way shows a good brightening effect.

EXAMPLE 15

Bleached wool fabric is treated for 60 minutes, using a liquor ratio of 1:40, in a bath which contains 0.1% of the brightener of the formula (44) or (49), calculated relative to the fibre weight and 4 g/l of hydrosulphite. After rinsing and drying, strong brightening effects of good fastness to light are obtained.

Strong brightening effects are also obtained if instead of the hydrosulphite 5% of acetic acid, calculated relative to the fibre weight are added to the bath.

EXAMPLE 16

10,000 g of a polyamide manufactured from hexamethylenediamine adipate in a known manner, in chip form are mixed for 12 hours in a tumbler vessel with 30 g of titanium oxide (rutile modification) and 5 g of one of the compounds of the formulae (38), (42), (43), (50), (73) or (78). The chips treated in this way are fused in a kettle heated to 300°–310° C with oil or diphenyl vapour, after displacing the atmospheric oxygen by steam, and the mixture is stirred for half an hour. Thereafter the melt is extruded through a spinneret under a nitrogen pressure of 5 atmospheres gauge and the filament which has been spun in this way and cooled is wound up on a spinning bobbin. The resulting filaments show a good brightening effect.

If instead of a polyamide manufactured from hexamethylenediamine adipate a polyamide manufactured from $\epsilon$-caprolactam is used, similarly good results are obtained.

EXAMPLE 17

An intimate mixture of 100 parts of polyvinyl chloride, 3 parts of stabiliser (Advastat BD 100; Ba/Cd complex), 2 parts of titanium dioxide, 59 parts of dioctyl phthalate and 0.01 to 0.2 part of one of the compounds of the formulae (38), (42), (52), (57), (65), (71), ((72) or (80) is milled on a calender at 150 to 155° C to give a film. The opaque polyvinyl chloride film thus obtained as a substantially higher degree of whiteness than a film which does not contain the optical brightener.

EXAMPLE 18

100 parts of polystyrene and 0.1 part of one of the compounds of the formulae (38), (52), (54), (58), (61) or (80) are fused, with exclusion of air, for 20 minutes at 210° C in a tube of 1 cm diameter. After cooling, an optically brightened polystyrene composition of good fastness to light is obtained.

EXAMPLE 19

100 g of polyester granules of terephthalic acid ethylene glycol polyester are initmately mixed with 0.05 g of one of the compounds of the formulae (42), (43) or (53) and fused at 285° C, whilst stirring. After spinning through the customary spinnerets, strongly brightened polyester fibres are obtained.

The compounds of the formulae (42), (43) or (53) can also be added to the starting substances before or during the polycondensation to give the polyester.

We claim:

1. Styryl compounds corresponding to the formula

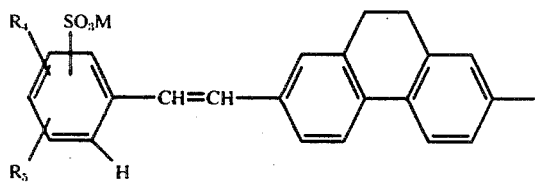

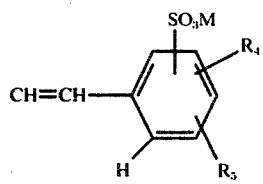

wherein $R_4$ denotes hydrogen, an alkyl group of 1 to 4 carbon atoms, an alkoxy group of 1 to 4 carbon atoms, or halogen, $R_5$ denotes hydrogen, an alkyl group with 1 to 4 carbon atoms, an alkoxy group with 1 to 4 carbon atoms, halogen, or $SO_3M$ and M represents a hydrogen ion or a salt-forming cation.

2. Styryl compounds according to claim 1, corresponding to the formula

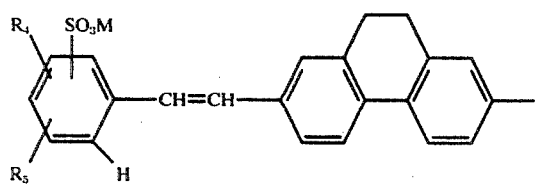

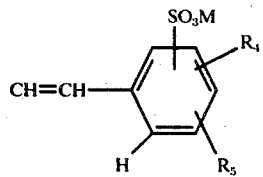

wherein $R_4$ denotes hydrogen, methyl, methoxy, or chlorine, $R_5$ denotes hydrogen, methyl, methoxy, chlorine or $SO_3M$ and M represents a hydrogen ion or salt-forming cation.

3. Styryl compounds according to claim 1, corresponding to the formula

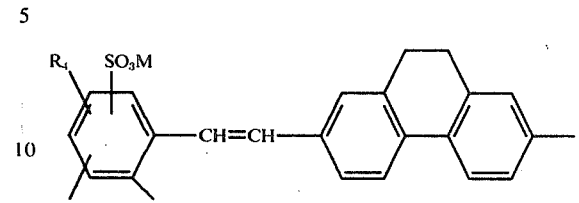

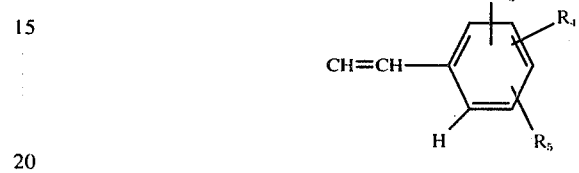

wherein $R_4$ denotes hydrogen, methyl, methoxy, or chlorine, $R_5$ denotes hydrogen, methyl, methoxy, chlorine or $SO_3M$ and M represents a hydrogen ion or salt-forming cation.

4. A styryl compound according to claim 1, corresponding to the formula

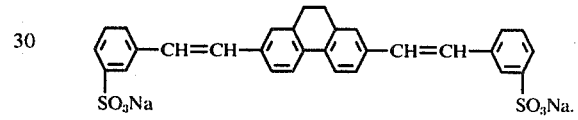

5. A styryl compound according to claim 1, corresponding to the formula

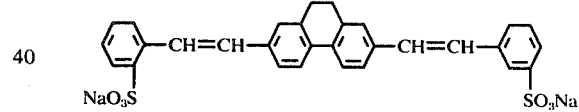

* * * * *

UNITED STATES PATENT OFFICE
CERTIFICATE OF CORRECTION

Patent No. 4,013,713   Dated March 22, 1977

Inventor(s) Kurt Weber et al.

It is certified that error appears in the above-identified patent and that said Letters Patent are hereby corrected as shown below:

Column 26, claim 3, lines 5-20, delete the structural formula as it now reads and insert

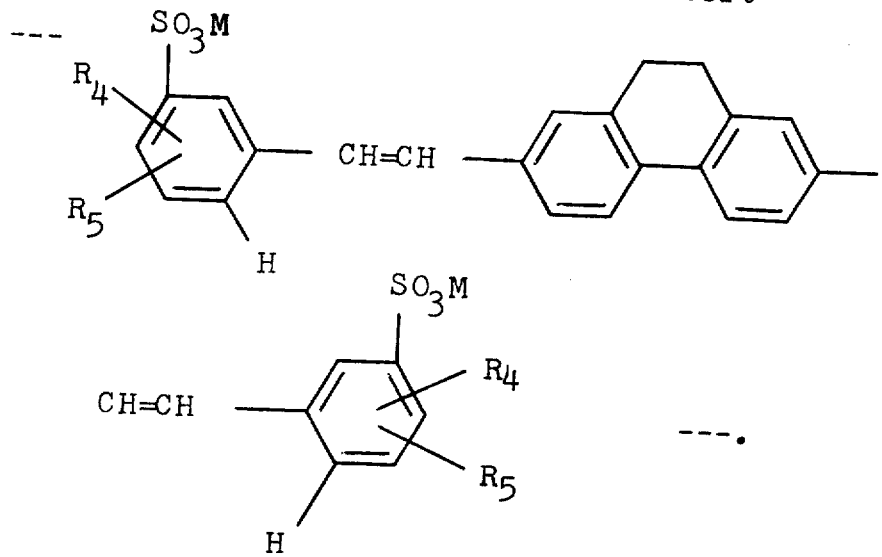

UNITED STATES PATENT OFFICE
CERTIFICATE OF CORRECTION

Patent No. 4,013,713   Dated March 22, 1977

Inventor(s) Kurt Weber et al.

It is certified that error appears in the above-identified patent and that said Letters Patent are hereby corrected as shown below:

Page 1, line 12, insert --- [30] Foreign application Priority Data

December 30, 1971  Switzerland . . . . 19173/71

Signed and Sealed this nineteenth Day of July 1977

[SEAL]

Attest:

RUTH C. MASON
*Attesting Officer*

C. MARSHALL DANN
*Commissioner of Patents and Trademarks*